United States Patent [19]

Fráter et al.

[11] Patent Number: 4,526,609
[45] Date of Patent: Jul. 2, 1985

[54] PHENOXY PHONOXY PROPIONIC HYDRAZIDES

[75] Inventors: Georg Fráter, Greifensee; Milos Suchy, Pfaffhausen; Jean Wenger, Uster; Paul Winternitz, Greifensee, all of Switzerland

[73] Assignee: Hoffmann-La Roche Inc., Nutley, N.J.

[21] Appl. No.: 380,654

[22] Filed: May 21, 1982

[30] Foreign Application Priority Data

May 26, 1981 [CH] Switzerland .......................... 3441/81
Mar. 31, 1982 [CH] Switzerland .......................... 1983/82

[51] Int. Cl.³ .................... A01N 37/18; C07C 103/22; C07C 103/30
[52] U.S. Cl. ....................................... 71/118; 564/150; 564/81; 260/453.7; 260/455 A; 260/453.1
[58] Field of Search ...................... 260/453.7; 564/150, 564/171, 174; 71/118

[56] References Cited

FOREIGN PATENT DOCUMENTS 0002800 12/1973 European Pat. Off. ............ 564/171
2278675 6/1975 France ................................. 564/171
2277811 6/1975 France ................................. 564/171
2042503 9/1980 United Kingdom ................ 564/171

Primary Examiner—Henry R. Jiles
Assistant Examiner—Robert C. Whittenbaugh
Attorney, Agent, or Firm—Jon S. Saxe; George M. Gould; John J. Maitner

[57] ABSTRACT

Propionic acid amides of the formula

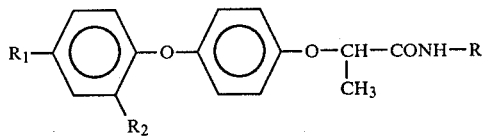

wherein
R, $R_1$ and $R_2$ are as defined hereinafter, processes for their preparation, herbicidal compositions containing these amides and methods of use of the herbicidal compositions are disclosed.

9 Claims, No Drawings

PHENOXY PHENORXY PROPIONIC HYDRAZIDES

SUMMARY OF THE INVENTION

The invention is directed to propionic acid amides of the formula

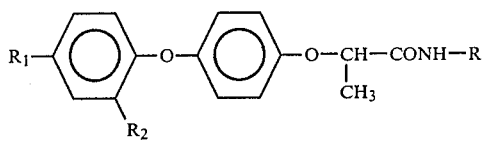
I wherein
R, $R_1$ and $R_2$ are as defined hereinafter, as well as processes for their preparation.

This invention is also directed to herbicidal compositions containing, as the active ingredient, a compound of formula I and methods for the use of these herbicidal compositions.

DETAILED DESCRIPTION OF THE INVENTION

The invention is directed to propionic acid amides of the formula

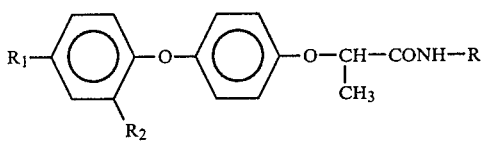
I wherein
$R_1$ is chlorine, iodine or trifluoromethyl,
$R_2$ is hydrogen or chlorine, and
R is one of the following groups (a)–(e):

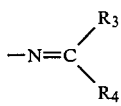 (a)

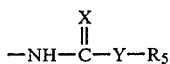 (b)

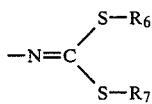 (c)

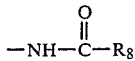 (d)

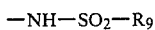 (e)

whereby in the above formulae of the groups (a)–(e)
$R_3$ and $R_4$ are hydrogen, $C_{1-4}$-alkyl, $C_{1-4}$-haloalkyl, phenyl, phenyl substituted with chlorine, methyl, methoxy and/or nitro, benzyl, benzyl substituted in the aryl nucleus with chlorine, methyl, methoxy and/or nitro, or together with the carbon atom to which they are attached form a $C_{5-7}$-cycloalkane ring, $R_5$ is $C_{1-4}$-alkyl, $C_{2-4}$-alkenyl, $C_{2-4}$-alkynyl, phenyl or benzyl, X and Y are oxygen or sulfur, $R_6$ and $R_7$ are $C_{1-4}$-alkyl, $C_{2-4}$-alkenyl, $C_{2-4}$-alkynyl, phenyl or benzyl or together form a $C_{2-4}$-alkylene group, with the proviso that $R_6$ and $R_7$ are not simultaneously phenyl;

$R_8$ is hydrogen, $C_{1-4}$-alkyl, $C_{1-4}$-haloalkyl, $C_{2-4}$-alkenyl, phenyl or phenyl substituted with chlorine, methyl, methoxy and/or nitro, and $R_9$ is $C_{1-4}$-alkyl, phenyl or phenyl substituted with chlorine, methyl, methoxy and/or nitro.

The invention is also directed to processes for the preparation of compounds of formula I, as well as herbicidal compositions and methods for their use, which contain, as the active ingredient, a compound of formula I. The compounds have both pre-emergence and post-emergence herbicidal activity.

In formula I above the term "$C_{1-4}$-alkyl" encompasses both straight- and branched-chain alkyl groups, such as methyl, ethyl, n-propyl, isopropyl, n-butyl, sec.-butyl, isobutyl and tert.butyl. This also applies for the haloalkyl groups containing $C_{1-4}$-alkyl groups.

The term "halogen" in the last-named groups includes fluorine, chlorine, bromine and iodine. In this connection, the term "haloalkyl" includes alkyl substituted with one or more halogen atoms, whereby when two or more halogen atoms are present they can be the same or different.

When two or more substituents are present in a substituted phenyl or benzyl group, the substituents can be the same or different. In the groups (a), (b) and (c) the definitions of $R_3$ and $R_4$, X and Y, or $R_6$ and $R_7$ are independent of one another.

Since the propionic acid amides of formula I have an asymmetric carbon atom, these compounds can exist in optically active isomeric forms. In fact, these amides can have more than one asymmetric carbon atom. The racemic compounds can be resolved into their dextrorotatory and laevorotatory isomers using known procedures as, for example, that described in Industrial and Engineering Chemistry 60 (8), 12–28 (1968). The optically active isomers can also be prepared from the corresponding optically active starting materials.

In addition, and as a result of the carbon-nitrogen double bond in the compounds of formula I wherein R is one of the groups (a) or (c), it is possible to have two geometric isomers when $R_3$ and $R_4$ or $R_6$ and $R_7$ are different. These geometric isomers, the syn- and anti-form, can also be isolated. Independently thereof, atropic isomerism is also present in certain cases. Formula I is intended to include the racemates as well as all of these possible isomeric forms.

Preferred compounds of formula I are those in which, independently of one another, $R_1$ denotes iodine or trifluoromethyl, $R_2$ denotes chlorine, and R denotes one of the groups (a),(b),(c) or (d). $R_3$ and $R_4$, independently of one another, in the group (a) preferably denote hydrogen, $C_{1-4}$-alkyl, $C_{1-4}$-haloalkyl, phenyl or phenyl substituted with chlorine, methyl, methoxy and/or nitro; $R_5$ in the group (b) preferably denotes $C_{1-4}$-alkyl; X and Y, independently of one another, in the group (b) preferably denote oxygen; $R_6$ and $R_7$, independently of one another, in the group (c) preferably denote $C_{1-4}$-alkyl, $C_{2-4}$-alkenyl or $C_{2-4}$-alkynyl; $R_8$ in the group (d) preferably denotes $C_{1-4}$-alkyl, $C_{1-4}$-haloalkyl, phenyl or phenyl substituted with chlorine, methyl, methoxy and/or nitro; and $R_9$ in the group (e) preferably denotes phenyl or phenyl substituted with chlorine, methyl, methoxy and/or nitro.

The D-forms of the compounds of formula I are especially preferred.

Preferred compounds of formula I are:

1-Isopropylidene-2-{D-2-[p-(α,α,α-trifluoro-p-tolyloxy)phenoxy]-propionyl}-hydrazine, 1-isopropylidene-2-{D-2-[p-(o-chloro-p-iodophenoxy)-phenoxy]-propionyl}-hydrazine, 1-isopropylidene-2-{D-2-[p-(o-chloro-α,α,α-trifluoro-p-tolyloxy)phenoxy]-propionyl}-hydrazine and ethyl 3-{D-2-[p-(o-chloro-α,α,α-trifluoro-p-tolyloxy)-phenoxy]-propionyl}-carbazate.

The compounds of formula I are prepared by one of the procedures described below.

A. Reacting an acid of the formula

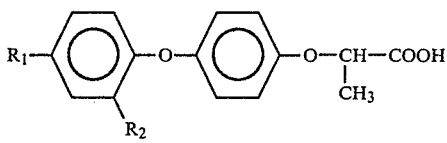  II wherein

R$_1$ and R$_2$ are as previously described, or a reactive derivative thereof such as a halide, for example the chloride, or the anhydride with a hydrazine derivative of the formula

H$_2$N—R   III wherein

R is as previously described.

This procedure involves an amidation reaction which can be carried out according to methods well known in the art. The reaction is preferably carried out in an inert solvent, at temperatures between 0° C. and the reflux temperature of the reaction mixture, preferably up to 50° C., and in the presence of a base or an acid-binding agent. Examples of solvents useful in carrying out this reaction are inert organic solvents, preferably hydrocarbons, for example, benzene, toluene, xylenes, and the like; chlorinated hydrocarbons, for example dichloromethane, chloroform and carbon tetrachloride; ethers and ether-like compounds, for example diethyl ether, tetrahydrofuran, and the like; and dimethylformamide. Suitable bases or acid-binding agents are inorganic bases, for example alkali metal and alkaline earth metal carbonates and bicarbonates, as well as organic bases, for example tertiary amines, preferably triethylamine and pyridine.

B. Reacting a hydrazide of the formula

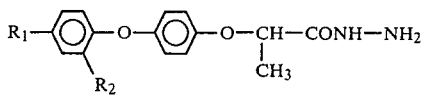  IV wherein

R$_1$ and R$_2$ are as previously described with an acid of the formula

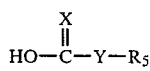  Va

HO—CO—R$_8$   Vb

HO—SO$_2$—R$_9$   Vc wherein

R$_5$, R$_8$, R$_9$, X and Y are as previously described, or a reactive derivative thereof, for example, a halide or the anhydride.

This procedure produces compounds of formula I wherein R denotes the group (b), (d) or (e). The reaction can be carried out according to methods well known in the art and is preferably carried out under the reaction conditions which are given above in connection with Procedure A.

C. Reacting a dithiocarbazic acid of the formula

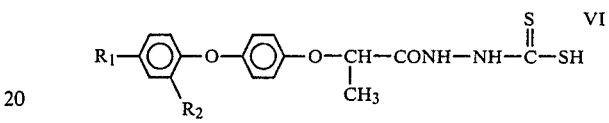  VI wherein

R$_1$ and R$_2$ are as previously described, or an alkali metal or alkaline earth metal salt thereof, as appropriate in the presence of a base or of an acid-binding agent, with a compound of the formula

R$_5$—Z$_1$   VII wherein

R$_5$ is as previously described and

Z$_1$ is a leaving group, for example, halogen or one equivalent of a sulfate group.

This procedure produces compounds of formula I wherein R is the group (b) and X and Y are both sulfur. The reaction is conveniently carried out in an inert solvent, such as a lower alkanol, water, an ether or an ether-like compound, for example, 1,2-dimethoxyethane, tetrahydrofuran, dioxan, or the like; dimethylformamide, N-methylpyrrolidone, or dimethyl sulphoxide. The reaction is conveniently carried out at temperatures between 0° C. and the reflux temperature of the reaction mixture, preferably between 20° C. and 50° C. Mixtures of the aforementioned organic solvents with water have been found to be especially suitable solvents for this reaction. Where the starting material of formula VI is not used in the form of a salt, namely an alkali metal or alkaline earth metal salt, the reaction is conveniently carried out in the presence of a base or of an acid-binding agent. Inorganic bases, for example, alkali metal and alkaline earth metal hydroxides and carbonates, as well as organic bases, for example, tertiary amines such as triethylamine and pyridine, are suitable for this reaction.

The starting material of formula VI used in procedure C can conveniently be prepared in situ by reacting a hydrazide of formula IV, as described above, with carbon disulfide, conveniently under the reaction conditions given above in connection with this procedure.

D. Reacting a dithiocarbazate of the formula

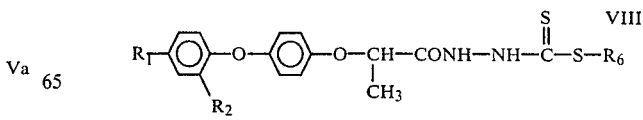  VIII wherein $R_1$, $R_2$ and $R_6$ are as previously described,
or an alkali metal or alkaline earth metal salt thereof, conveniently in the presence of a base, with a compound of the formula $$R_7 - Z_1 \qquad \text{IX}$$

wherein $R_7$ and $Z_1$ are as previously described.

This procedure produces compounds of formula I wherein R is the group (c). The reaction is preferably carried out under the same reaction conditions as described above for Procedure C.

E. Reacting a hydrazide of formula IV, as described above, with an aldehyde or ketone of the formula

X wherein $R_3$ and $R_4$ are as previously described.

This procedure produces compounds of formula I wherein R is the group (a). The reaction is conveniently carried out by reacting the starting materials for formulae IV and X, optionally in the presence of an acid catalyst, for example, p-toluenesulphonic acid, in an inert organic solvent. Examples of suitable solvents for this reaction are hydrocarbons, for example, benzene, toluene and xylenes; chlorinated hydrocarbons, for example, dichloromethane, chloroform and carbon tetrachloride; and ethers and ether-like compounds, for example, diethyl ether, tetrahydrofuran and dioxane. The starting material of formula X can itself in certain cases advantageously also be used as the solvent. The reaction is preferably carried out in a temperature range between room temperature and the reflux temperature of the reaction mixture, preferably between about 20° C. and about 50° C.

F. Reacting a phenol of the formula

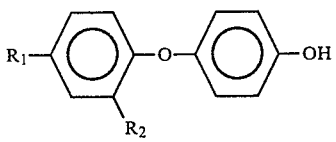

XI wherein $R_1$ and $R_2$ are as previously described,
or an alkali metal salt thereof, conveniently in the presence of a base or of an acid-binding agent, with a hydrazine derivative of the formula

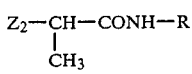

XII wherein

R is as previously described and $Z_2$ is a leaving group, preferably chlorine, bromine, iodine, mesyloxy or toxyloxy.

This reaction is preferably carried out in a basic medium. Examples of basic media useful in this reaction are inorganic bases, for example, sodium and potassium hydroxide and sodium carbonate and bicarbonate, as well as organic bases, for example, tertiary amines, preferably triethylamine and pyridine. In many cases it is convenient to carry out the reaction in the presence of an inert organic solvent, such as an ether or an ether-like compound, for example, diethyl ether, tetrahydrofuran or dioxan, dimethylformamide, N-methylpyrrolidone, or hexamethylphosphoric acid triamide. The reaction can be carried out over a temperature range of from about room temperature to the boiling temperature of the reaction mixture, preferably between about 20° C. and about 50° C.

Examples of alkali metal or alkaline earth metal salts of the corresponding starting materials of formulae VI, VIII and XI which can be used in procedures C, D and F are the sodium, potassium, calcium and magnesium salts, and preferably the sodium and potassium salts.

The starting materials of formulae II, III, IV, Va, Vb, Vc, VII, IX, X, XI and XII, as well as reactive derivatives of the acids of formulae II, Va, Vb and Vc and alkali metal salts of the phenols of formula XI, are either known or can be prepared by conventional procedures. The starting materials of formula VI, i.e. the dithiocarbazic acids, can be prepared, for example, as described above in connection with procedure C. The starting materials of formula VIII correspond to the end products of formula I in which R is the group (b), X and Y both being sulfur and $R_5$ is the same as $R_6$. Such starting materials can be prepared, for example, according to procedures A, B, C and F given above from corresponding starting materials, and their alkali metal and alkaline earth metal salts can be prepared in a manner known per se.

The compounds of formula I are useful as both pre-emergent and post-emergent herbicides. They are particularly suitable in combatting weed grasses such as millet, wild oats, foxtail grass, couch grass, and aleppo grass in dicotyledonous crops and in cereals. They are suitable for use against these weed grasses especially soya, cotton, sugar beet, potato, rape, rice and cereal crops. The compounds of formula I are particularly useful for the control of weed grasses in soya, cotton, sugar beet and rice crops.

In general, the compounds of formula I are effective as herbicides when applied at a concentration of about 0.1 to about 2.0 kg/ha with the preferred concentration range being from about 0.25 to about 1.0 kg/ha.

The invention is also directed to herbicidal compositions which comprise inert carrier material and, as the active ingredient, one or more compounds of formula I. These herbicidal compositions suitably contain, as the inert carrier material, at least one of the following ingredients: solid carrier materials, solvents or dispersion media, tensides (wetting and emulsifying agents), dispersing agents (without tenside action) and stabilizers. The herbicidal compositions of this invention can be formulated in the usual forms, for example dusts, powders, granulates, solutions, emulsions, suspensions, emulsifiable concentrates, pastes, and the like.

The compounds of formula I are in general water-insoluble. Thus, the usual methods of formulation of insoluble materials can be employed. For example, the compounds can be mixed with solid carrier substances, dissolved or suspended in suitable solvents or dispersion media, if necessary using tensides as wetting or emulsifying agents and/or dispersing agents, diluting pre-prepared emusifiable concentrates with solvents or dispersion media, etc.

Suitable solid carrier materials include natural substances, such as chalk, dolomite, limestone, aluminas, and silicic acid and salts thereof, for example, siliceous earth, kaolin, bentonite, talc, attapulgite and montmorillonite; synthetic mineral substances, such as highly dispersible silicic acid, aluminum oxide and silicates; organic substances, such as cellulose, starch, urea and synthetic resins; and fertilizers, such as phosphates and nitrates. The solid carrier substances can be present as powders or as granulates.

Suitable solvents or dispersion media include aromatic hydrocarbons, such as benzene, toluene, xylenes and alkylnaphthalenes; chlorinated aromatic and chlorinated aliphatic hydrocarbons, such as chlorobenzenes, chloroethylenes and methylene chloride; aliphatic hydrocarbons, such as cyclohexane and paraffins, for example, petroleum fractions; alcohols, such as butanol and glycol, as well as their ethers and esters; ketones, such as acetone, methyl ethyl ketone, methyl isobutyl ketone and cyclohexanone; and strongly polar solvents or dispersion media such as dimethylformamide, N-methylpyrrolidone and dimethyl sulphoxide, whereby such solvents or dispersion media preferably have flash points of a least 30° C. and boiling points of at least 50° C., and water. Also included in the solvents or dispersion media which can be used in preparing the herbicidal compositions are the so-called liquified gaseous extenders or carrier substances, these being products which are gaseous at room temperature and under normal pressure. Examples of such products are aerosol propellant gases such as halogenated hydrocarbons, for example, dichlorodifluoromethane. If a weed control composition in accordance with the invention is present in the form of a pressurized pack, then a solvent is conveniently used in addition to the propellant gas.

Tensides (wetting and emulsifying agents) suitable for use with the compounds of this invention can be anionic, cationic or nonionic.

Examples of anionic tensides include soaps; fatty sulfate esters, such as dodecyl sodium sulfate, octadecyl sodium sulfate and cetyl sodium sulfate; alkyl sulfonates, aryl sulfonates and fatty-aromatic sulfonates, such as alkylbenzene-sulfonates, for example, calcium dodecylbenzene sulfonate, and butylnaphthalene-sulfonates; and the more complex fatty sulfonates, such as the amide condensation products of oleic acid and N-methyltaurine or the sodium sulfonate of dioctyl succinate.

Examples of nonionic tensides include, for example, condensation products of fatty acids, fatty alcohols or fatty-substituted phenols with ethylene oxide; fatty acid esters and ethers of sugars or polyhydric alcohols; condensation products of sugars or polyhydric alcohols with ethylene oxide; block copolymers of ethylene oxide and propylene oxide, or alkyldimethylamine oxides.

Examples of cationic tensides include alkyldimethylbenzylammonium chlorides, dialkyldimethylammonium chlorides, alkyltrimethylammonium chlorides and ethoxylated quaternary ammonium chlorides.

Suitable dispersing agents (without tenside action) include lignin, sodium and ammonium salts of lignin sulphonic acids, sodium salts of maleic acid anhydride/diisobutylene copolymers, sodium and ammonium salts of sulphonated polycondensation products of naphthalene and formaldehyde, and sulphite lyes.

Dispersing agents which are especially suitable as thickening agents or antisettling agents include methylcellulose, carboxymethylcellulose, hydroxyethylcellulose, polyvinyl alcohol, alginates, caseinates and blood albumin.

Examples of suitable stablizers are acid-binding agents, for example, epichlorohydrin, phenyl glycidyl ether, soya epoxides and the like; antioxidants, for example, gallic acid esters, butylhydroxytoluene and the like; UV-absorbers, for example, substituted benzophenones, diphenylacrylonitrile acid esters, cinnamic acid esters and the like; and deactivators, for example, salts of ethylenediaminotetraacetic acid, polyglycols and the like.

The herbicidal compositions of this invention can also contain, in addition to the compounds of formula I, synergistic agents and other active ingredients, such as insecticides, acaricides, bactericides, other herbicides, fungicides, plant growth regulators and fertilizers. Such combination preparations are suitable for increasing the activity or for broadening the spectrum of activity.

The herbicidal compositions of this invention generally contain between 0.01 and 90 percent by weight, preferably between 25 and 75 percent by weight, of one or more compounds of formula I as the active ingredient. The composition can be in the form of emulsifiable concentrates suitable for storage and shipment. In such concentrate formulations the active substance concentration is normally in the higher range, preferably between 25 and 75 percent by weight, especially between 40 and 60 percent by weight. These formulations can subsequently be diluted, for example, with the same or different inert ingredients, to give active ingredient concentrations which are suitable for practical use, i.e. preferably about 0.05 and 5 percent by weight, especially about 0.1 to 1 percent by weight. The active ingredient concentrations can, however, also be smaller or greater.

The herbicidal compositions of this invention can be prepared according to known formulation procedures.

For the preparation of pulverous preparations, the active ingredient, i.e. at least one compound of formula I, can be mixed with solid carrier materials, for example, by grinding the ingredients together, or the solid carrier material can be impregnated with a solution or suspension of the active ingredient and then the solvent or dispersion medium can be removed by evaporation, heating, or by vacuum reduced pressure. By adding tensides or dispersing agents, such pulverous preparations can be made readily wettable with water, so that they can be converted into aqueous suspensions which are suitable, for example, as spray compositions.

The compounds of formula I can also be mixed with a tenside and a solid carrier material to form a wettable powder which is dispersible in water, or they can be mixed with a solid pre-granulated carrier material to form a granulate.

If desired, the compounds of formula I can be dissolved in a water-immiscible solvent, such as, for example, a high-boiling hydrocarbon, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active ingredient can be dissolved in a solvent, and thereafter the solution can be mixed with an emulsifying agent. Such a mixture can likewise be diluted with water to the desired concentration. In this matter there are obtained emulsifiable concentrates or ready-for-use emulsions.

The use of the herbicidal compositions of this invention can be carried out according to usual application methods, such as sprinkling, spraying, dusting, pouring or scattering. The method of this invention for the control of weeds comprises treating the locus to be protected against weeds and/or the weeds with a compound of formula I or with a herbicidal composition in accordance with the invention.

The following Examples illustrate the invention.

EXAMPLE 1

A solution of 34.4 g of D-2-[p-($\alpha,\alpha,\alpha$-trifluoro-p-tolyloxy)phenoxy]-propionyl chloride in 100 ml of benzene is added dropwise while stirring at 40° C. during 30 minutes to a solution of 12.2 g of methyl hydrazinedithiocarboxylate and 9.5 g of pyridine in 200 ml of benzene. The solvent is distilled off in vacuo, the residue is dissolved in 300 ml of ethyl acetate, and the solution is extracted with water, dried over anhydrous sodium sulfate, and evaporated to dryness. The residue is dissolved in 50 ml of diethyl ether, the solution is treated portionwise with 400 ml of n-hexane, and the resulting precipitate is isolated by filtration to yield methyl 3-{D-2-[p-($\alpha,\alpha,\alpha$-trifluoro-p-tolyloxy)phenoxy]-propionyl}-dithiocarbazate; m.p. 126°–128° C.; $[\alpha]_D^{22} = +71.8°$ (c=1.2% in CHCl$_3$).

Following analogous procedures, the following compounds are prepared:

(a) methyl 3-{D-2-[p-(p-iodophenoxy)phenoxy]-propionyl}-dithiocarbazate; m.p. 135°–138° C.; $[\alpha]_D^{22} = +51.3°$ (c=1.3% in CHCl$_3$) from methyl hydrazinedithiocarboxylate and D-2-[p-(p-iodophenoxy)phenoxy]-propionyl chloride.

(b) benzyl 3-{D-2-[p-($\alpha,\alpha,\alpha$-trifluoro-p-tolyloxy)phenoxy]-propionyl}-dithiocarbazate; m.p. 119°–122° C.; $[\alpha]_D^{22} = +57.9°$ (c=1.0% in CHCl$_3$) from benzyl hydrazinedithiocarboxylate and D-2-[p-($\alpha,\alpha,\alpha$-trifluoro-p-tolyloxy)phenoxy]-propionyl chloride.

EXAMPLE 2

A solution of 3.4 g of D-2-[p-($\alpha,\alpha,\alpha$-trifluoro-p-tolyloxy)phenoxy]-propionic acid hydrazide in 20 ml of dichloromethane is treated with 2.0 g of acetic anhydride. The precipitated crystals are filtered off under suction and recrystallized from dichloromethane/n-hexane to yield 1-acetyl-2-{D-2-[p-($\alpha,\alpha,\alpha$-trifluoro-p-tolyloxy)phenoxy]-propionyl}-hydrazine; m.p. 178°–180° C.; $[\alpha]_D^{22} = +19.2°$ (c=1.2% in C$_2$H$_5$OH).

Following analogous procedures, the following compound is prepared:

(a) 1-chloroacetyl-2-{D-2-[p-($\alpha,\alpha,\alpha$-trifluoro-p-tolyloxy)phenoxy]-propionyl}-hydrazine; m.p. 192°–194° C.; $[\alpha]_D^{22} = +20.5°$ (c=0.9% in C$_2$H$_5$OH) from D-2-[p-($\alpha,\alpha,\alpha$-trifluoro-p-tolyloxy)phenoxy]-propionic acid hydrazide and chloroacetic anhydride.

EXAMPLE 3

A solution of 3.4 g of D-2-[p-($\alpha,\alpha,\alpha$-trifluoro-p-tolyloxy)phenoxy]-propionic acid hydrazide and 1.7 g of benzoyl chloride in 40 ml of dichloromethane is treated at 10° C. with 1.6 g of pyridine, and the mixture is left to stand at 20° C. for 15 hours. The mixture is then evaporated in vacuo, the solid residue is dissolved in 100 ml of diethyl ether, and the solution is extracted with water, dried over anhydrous sodium sulfate, and evaporated to dryness. The residue is crystallized from diethyl ether/n-hexane to yield 1-benzoyl-2-{D-2-[p-($\alpha,\alpha,\alpha$-trifluoro-p-tolyloxy)phenoxy]-propionyl}-hydrazine; m.p. 158°–160° C.; $[\alpha]_D^{22} = +14.8°$ (c=0.7% in CHCl$_3$).

Following analogous procedures, the following compounds are prepared.

(a) 1-methanesulphonyl-2-{D-2-[p-($\alpha,\alpha,\alpha$-trifluoro-p-tolyloxy)phenoxy]-propionyl}-hydrazine; m.p. 125°–128° C.; $[\alpha]_D^{22} = -20.0°$ (c=1.4% in C$_2$H$_5$OH) from D-2-[p-($\alpha,\alpha,\alpha$-trifluoro-p-tolyloxy)phenoxy]-propionic acid hydrazide and methanesulphonyl chloride.

(b) 1-(toluene-4-sulphonyl)-2-{D-2-[p-($\alpha,\alpha,\alpha$-trifluoro-p-tolyloxy)phenoxy]-propionyl}-hydrazine; m.p. 165°–168° C.; $[\alpha]_D^{22} = +55.6°$ (c=1.0% in C$_2$H$_5$OH) from D-2-[p-($\alpha,\alpha,\alpha$-trifluoro-p-tolyloxy)phenoxy]-propionic acid hydrazide and toluene-4-sulphonyl chloride.

(c) ethyl 3-{D-2-[p-($\alpha,\alpha,\alpha$-trifluoro-p-tolyloxy)phenoxy]-propionyl}-carbazate; m.p. 84°–91° C.; $[\alpha]_D^{22} = -4.0°$ (c=0.8% in CHCl$_3$) from D-2-[p-($\alpha,\alpha,\alpha$-trifluoro-p-tolyloxy)phenoxy]-propionic acid hydrazide and ethyl chloroformate.

(d) 1-benzoyl-2-{D-2-[p-(p-iodophenoxy)phenoxy]-propionyl}-hydrazine; m.p. 182°–184° C.; $[\alpha]_D^{22} = +10.4°$ (c=2.2% in CHCl$_3$) from D-2-[p-(p-iodophenoxy)phenoxy]-propionic acid hydrazide and benzoyl chloride.

(e) ethyl 3-{D-2-[p-(p-iodophenoxy)phenoxy]-propionyl}-carbazate; m.p. 107°–108° C.; $[\alpha]_D^{22} = -3.0°$ (c=1.3% in CHCl$_3$) from D-2-[p-(p-iodophenoxy)phenoxy]-propionic acid hydrazide and ethyl chloroformate.

(f) 1-benzoyl-2-{D-2-[p-(o-chloro-p-iodophenoxy)phenoxy]-propionyl}-hydrazine; m.p. 170°–172° C.; $[\alpha]_D^{22} = +10.7°$ (c=1.6% in CHCl$_3$) from D-2-[p-(o-chloro-p-iodophenoxy)phenoxy]-propionic acid hydrazide and benzoyl chloride.

(g) ethyl 3-{D-2-[p-(o-chloro-p-iodophenoxy)phenoxy]-propionyl}-carbazate; m.p. 115°–118° C.; $[\alpha]_D^{22} = -2.2°$ (c=1.5% in CHCl$_3$) from D-2-[p-(o-chloro-p-iodophenoxy)phenoxy]-propionic acid hydrazide and ethyl chloroformate.

(h) 1-benzoyl-2-{D-2-[p-(o-chloro-$\alpha,\alpha,\alpha$-trifluoro-p-tolyloxy)phenoxy]-propionyl}-hydrazine; m.p. 139°–144° C.; $[\alpha]_D^{22} = +15.1°$ (c=0.95% in CHCl$_3$) from D-2-[p-(o-chloro-$\alpha,\alpha,\alpha$-trifluoro-p-tolyloxy)phenoxy]-propionic acid hydrazide and benzoyl chloride.

(i) ethyl 3-{D-2-[p-(o-chloro-$\alpha,\alpha,\alpha$-trifluoro-p-tolyloxy)phenoxy]-propionyl}-carbazate; $[\alpha]_D^{22} = -3.3°$ (c=0.94% in CHCl$_3$) from D-2-[p-(o-chloro-$\alpha,\alpha,\alpha$-trifluoro-p-tolyloxy)phenoxy]-propionic acid hydrazide and ethyl chloroformate.

EXAMPLE 4

A solution of 4.3 g of methyl 3-{D-2-[p-($\alpha,\alpha,\alpha$-trifluoro-p-tolyloxy)phenoxy]-propionyl}-dithiocarbazate and 1.5 g of sodium carbonate in 125 ml of water and 75 ml of methanol is treated at 25° C. with 4.2 g of methyl iodide, and the mixture is stirred at 35° C. for 1 hour. The precipitated crystals are filtered off under suction, washed with water, and dissolved in diethyl ether. Thereafter the solution is dried over anhydrous sodium sulfate and concentrated to 10 ml, and crystallation is brought about using a small amount of n-hexane. In this manner there are obtained crystals of dimethyl N-{D-2-[p-($\alpha,\alpha,\alpha$-trifluoro-p-tolyloxy)phenoxy]-propionamido}-dithioimidocarbonate; m.p. 97°–99° C.; $[\alpha]_D^{22} = +63.2°$ (c=1.6% in CHCl$_3$).

Following analogous procedures, the following compounds are prepared.

(a) methyl(2-propynyl)N-{D-2-[p-(p-iodophenoxy)-phenoxy]-propionamido}-dithioimidocarbonate; $n_D^{30}=1.6500$; $[\alpha]_D^{22}=+34.1°$ (c=0.8% in CHCl$_3$) from methyl 3-{D-2-[p-(p-iodophenoxy)phenoxy]-propionyl}-dithiocarbazate and propargyl bromide using aqueous 1,2-dimethoxyethane as the solvent.

(b) ethyl methyl N-{D-2-[p-($\alpha,\alpha,\alpha$-trifluoro-p-tolyloxy)phenoxy]-propionamido}-dithioimidocarbonate; m.p. 73°–76° C.; $[\alpha]_D^{22}=+55.0°$ (c=1.2% in CHCl$_3$) from methyl 3-{D-2-[p-($\alpha,\alpha,\alpha$-trifluoro-p-tolyloxy)-phenoxy]-propionyl}-dithiocarbazate and ethyl bromide.

(c) methyl(2-propynyl)N-{D-2-[p-($\alpha,\alpha,\alpha$-trifluoro-p-tolyloxy)phenoxy]-propionamido}-dithioimidocarbonate; $[\alpha]_D^{22}=+54.4°$ (c=0.8% in CHCl$_3$) from methyl 3-{D-2-[p-($\alpha,\alpha,\alpha$-trifluoro-p-tolyloxy)-phenoxy]-propionyl}-dithiocarbazate and propargyl bromide.

(d) isopropyl methyl N-{D-2-[p-($\alpha,\alpha,\alpha$-trifluoro-p-tolyloxy)phenoxy]-propionamido}-dithioimidocarbonate; $n_D^{30}=1.5642$; $[\alpha]_D^{22}=+46.0°$ (c=1.2% in CHCl$_3$) from methyl 3-{D-2-[p-($\alpha,\alpha,\alpha$-trifluoro-p-tolyloxy)phenoxy]-propionyl}-dithiocarbazate and isopropyl bromide.

(e) benzyl methyl N-{D-2-[p-($\alpha,\alpha,\alpha$-trifluoro-p-tolyloxy)phenoxy]-propionamido}-dithioimidocarbonate; $n_D^{30}=1.5936$; $[\alpha]_D^{22}=+55.2°$ (c=1.0% in CHCl$_3$) from methyl 3-{D-2-[p-($\alpha,\alpha,\alpha$-trifluoro-p-tolyloxy)-phenoxy]-propionyl}-dithiocarbazate and benzyl bromide.

(f) allyl methyl N-{D-2-[p-($\alpha,\alpha,\alpha$-trifluoro-p-tolyloxy)-phenoxy]-propionamido}-dithioimidocarbonate; $n_D^{30}=1.5795$; $[\alpha]_D^{22}=+24.8°$ (c=1.1% in CHCl$_3$) from methyl 3-{D-2-[p-($\alpha,\alpha,\alpha$-trifluoro-p-tolyloxy)-phenoxy]-propionyl}-dithiocarbazate and allyl bromide.

EXAMPLE 5

A mixture of 34.0 g of methyl D-2-[p-($\alpha,\alpha,\alpha$-trifluoro-p-tolyloxy)phenoxy]-propionate and 25 g of hydrazine hydrate is stirred at 90° C. for 4 hours. After cooling, the resulting crystal slurry is extracted with 1 liter of diethyl ether and the ether phase is washed with water, dried over anhydrous sodium sulfate and evaporated to dryness. The residue is crystallized from diethyl ether/n-pentane to yield D-2-[p-($\alpha,\alpha,\alpha$-trifluoro-p-tolyloxy)phenoxy]-propionic acid hydrazide; m.p. 94°–96° C.; $[\alpha]_D^{20}=-20.0°$ (c=1.2% in CHCl$_3$).

A solution of 3.4 g of D-2-[p-($\alpha,\alpha,\alpha$-trifluoro-p-tolyloxy)phenoxy]-propionic acid hydrazide and 0.05 g of p-toluenesulphonic acid in 25 ml of anhydrous acetone is left to stand at 25° C. for 10 hours. Thereafter the mixture is evaporated to dryness and the residue is purified by chromatography on silica gel with dichloromethane/acetone (4:1) to yield 1-isopropylidene-2-{D-2-[p-($\alpha,\alpha,\alpha$-trifluoro-p-tolyloxy)phenoxy]-propionyl}-hydrazine; m.p. 93°–95° C.; $[\alpha]_D^{22}$ +50.7° (c=0.8% in CHCl$_3$).

Following analogous procedures, the following compounds are prepared:

(a) 1-(1-isopropyl-2-methylpropylidene)-2-{D-2-[p-($\alpha,\alpha,\alpha$-trifluoro-p-tolyloxy)phenoxy]-propionyl}-hydrazine; m.p. 99°–102° C.; $[\alpha]_D^{22}=+15.52°$ (c=1.2% in CHCl$_3$) from D-2-[p-($\alpha,\alpha,\alpha$-trifluoro-p-tolyloxy)phenoxy]-propionic acid hydrazide and diisopropyl ketone.

(b) 1-(2,2,2-trichloroethylidene)-2-{D-2-[p-($\alpha,\alpha,\alpha$-trifluoro-p-tolyloxy)phenoxy]-propionyl}-hydrazine; m.p. 122°–125° C.; $[\alpha]_D^{22}=-27.7°$ (c=0.9% in CHCl$_3$) from D-2-[-p-($\alpha,\alpha,\alpha$-trifluoro-p-tolyloxy)-phenoxy]-propionic acid hydrazide and freshly distilled trichloro-acetaldehyde using dichloromethane as the solvent.

(c) 1-cyclohexylidene-2-{D-2-[p-($\alpha,\alpha,\alpha$-trifluoro-p-tolyloxy)phenoxy]-propionyl}-hydrazine; m.p. 122°–124° C.; $[\alpha]_D^{22}=+57.7°$ (c=0.6% in CHCl$_3$) from D-2-[p-($\alpha,\alpha,\alpha$-trifluoro-p-tolyloxy)phenoxy]-propionic acid hydrazide and cyclohexane using dichloromethane as the solvent.

(d) 1-benzylidene-2-{D-2-[p-($\alpha,\alpha,\alpha$-trifluoro-p-tolyloxy)phenoxy]-propionyl}-hydrazine; m.p. 174°–177° C.; $[\alpha]_D^{22}=-57.8°$ (c=1.0% in CHCl$_3$) from D-2-[p-($\alpha,\alpha,\alpha$-trifluoro-p-tolyloxy)phenoxy]-propionic acid hydrazide and benzaldehyde using dichloromethane as the solvent.

(e) 1-($\alpha$-methylbenzylidene)-2-{D-2-[p-($\alpha,\alpha,\alpha$-trifluoro-p-tolyloxy)phenoxy]-propionyl}-hydrazine; m.p. 99°–101° C.; $[\alpha]_D^{22}=-79.3°$ (c=0.6% in CHCl$_3$) from D-2-[p-($\alpha,\alpha,\alpha$-trifluoro-p-tolyloxy)phenoxy]-propionic acid hydrazide and acetophenone using dichloromethane as the solvent.

(f) 1-isopropylidene-2-{D-2-[p-(o-chloro-p-iodophenoxy)phenoxy]-propionyl}-hydrazine; $[\alpha]_D^{22}=+50.9°$ (c=1.1% in CHCl$_3$) from D-2-[p-(o-chloro-p-iodophenoxy)phenoxy]-propionic acid hydrazide and acetone.

(g) 1-isopropylidene-2-{D-2-[p-(p-iodophenoxy)-phenoxy]-propionyl}-hydrazine; $[\alpha]_D^{22}=+48.3°$ (c=1.1% in CHCl$_3$) from D-2-[p-(p-iodophenoxy)-phenoxy]-propionic acid hydrazide and acetone.

(h) 1-isopropylidene-2-{D-2-[p-(o-chloro-$\alpha,\alpha,\alpha$-trifluoro-p-tolyloxy)phenoxy]-propionyl}-hydrazine; m.p. 115°–119° C.; $[\alpha]_D^{22}=+50.04°$ (c=1.23% in CHCl$_3$) from D-2-[p-(o-chloro-$\alpha,\alpha,\alpha$-trifluoro-p-tolyloxy)phenoxy]propionic acid hydrazide and acetone.

The starting materials D-2-[p-(o-chloro-p-iodophenoxy)phenoxy]-propionic acid hydrazide [m.p. 98°–102° C.; $[\alpha]_D^{20}=-13.0°$ (c=1.2% in CHCl$_3$)], D-2-[p-(p-iodophenoxy)-phenoxy]-propionic acid hydrazide and D-2-[p-(o-chloro-$\alpha,\alpha,\alpha$-trifluoro-p-tolyloxy)-phenoxy]-propionic acid hydrazide [m.p. 105°–108° C.; $[\alpha]_D^{22}=-15.3°$ (c=0.84% in CHCl$_3$)], which are used in the above process, are prepared in an analogous manner to the above-described process for the preparation of D-2-[p-($\alpha,\alpha,\alpha$-trifluoro-p-tolyloxy)phenoxy]-propionic acid hydrazide, namely from methyl D-2-[p-(o-chloro-p-iodophenoxy)phenoxy]-propionate or methyl D-2-[p-(p-iodophenoxy)phenoxy]-propionate or methyl D-2-[p-(o-chloro-$\alpha,\alpha,\alpha$-trifluoro-p-tolyloxy)phenoxy]-propionate and hydrazine hydrate.

EXAMPLE 6

This Example illustrates the preparation of an emulsifiable concentrate with a compound of this invention. The following ingredients are admixed:

| Ingredient | Amount |
|---|---|
| Compound of formula I | 500 g |
| Mixture of condensation products of an alkylphenol and ethylene oxide and calcium dodecylbenzenesulphonate | 100 g |
| Epoxidated soya oil with and oxirane oxygen content of about 6% | 25 g |

| Ingredient | Amount |
| --- | --- |
| Butylated hydroxytoluene | 10 g |

The mixture is made up to 1 liter with xylene.

The concentrate emulsifies spontaneously in water. The resulting emulsion is suitable as a ready-for-use spray liquor.

EXAMPLE 7

This Example illustrates the preparation of an emulsifiable concentrate with a compound of this invention.

The following ingredients are admixed:

| Ingredient | Amount |
| --- | --- |
| Compound of formula I | 250 g/l |
| N—methyl-2-pyrrolidone | 300 g/l |
| Emulsifier A[(1)] | 100 g/l |
| Emulsifier B[(2)] | 25 g/l |
| Solvent mixture of alkylbenzenes to | 1000 ml |

[(1)]Emulsifier A: Emulsifier consisting of 60 parts of a block polymerizate of ethylene oxide and propylene oxide, 20 parts of the calcium salt of a branched-chain dodecylbenzenesulphonic acid and 20 parts of a solvent mixture of isobutanol and $C_{10}$-alkylbenzenes.

[(2)]Emulsifier B: Mixture of 70 parts of the calcium salt of a branched-chain dodecylbenzenesulphonic acid and 30 parts of a solvent mixture of isobutanol and $C_{10}$-alkylbenzenes.

The concentrate emulsifies spontaneously in water. The resulting emulsion is suitable as a ready-for-use spray liquor.

We claim:

1. A compound of the formula

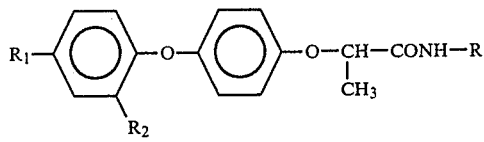

wherein
$R_1$ is chlorine, iodine or trifluoromethyl,
$R_2$ is hydrogen or chlorine and
R is the group:

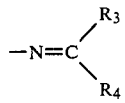

wherein
$R_3$ and $R_4$ are hydrogen, $C_{1-4}$-alkyl, $C_{1-4}$-haloalkyl, phenyl, phenyl substituted with chlorine, methyl, methoxy and/or nitro, benzyl, benzyl substituted in the aryl nucleus with chlorine, methyl, methoxy and/or nitro, or together with the carbon atom to which they are attached from a $C_{5-7}$-cycloalkane ring.

2. The compound defined in claim 1, wherein $R_1$ is iodine or trifluoromethyl.

3. The compound defined in claim 2, wherein $R_1$ is iodine and $R_2$ is chlorine.

4. The compound defined in claim 2, wherein $R_1$ is trifluoromethyl and $R_2$ is chlorine.

5. The D-forms of the compounds according to claim 1.

6. A compound defined in claim 1, selected from the group consisting of
1-(1-isopropyl-2-methylpropylidene)-2-{D-2-[p-(α,α,α-trifluoro-p-tolyloxy)-phenoxy]-propionyl}-hydrazine,
1-(2,2,2-trichloroethylidene)-2-{D-2-[p-(α,α,α-trifluoro-p-tolyloxy)phenoxy]-propionyl}-hydrazine,
1-cyclohexylidene)-2-{D-2-[p-(α,α,α-trifluoro-p-tolyloxy)phenoxy]-propionyl}-hydrazine,
1-benzylidene-2-{D-2-[p-(α,α,α-trifluoro-p-tolyloxy)phenoxy]-propionyl}-hydrazine, and
1-(α-methylbenzylidene)-2-{D-2-[p-(α,α,α-trifluoro-p-tolyloxy)phenoxy]-propionyl}-hydrazine.

7. A compound defined in claim 1, selected from the group consisting of 1-isopropylidene-2-{D-2-[p-(p-iodophenoxy)phenoxy]-propionyl}-hydrazine.

8. A herbicidal composition which comprises inert carrier material and, as the active ingredient, an amount of one or more of the compounds of claim 1 which is effective as a herbicide.

9. A method for combatting weeds which comprises applying to the locus to be protected, a herbicidally effective amount of the composition of claim 8.

* * * * *